(12) United States Patent
Leven et al.

(10) Patent No.: US 12,011,604 B2
(45) Date of Patent: *Jun. 18, 2024

(54) OPTICAL STIMULATION SYSTEM WITH ON-DEMAND MONITORING AND METHODS OF MAKING AND USING

(71) Applicant: Boston Scientific Neuromodulation Corporation, Valencia, CA (US)

(72) Inventors: Jacob B. Leven, Huntington Beach, CA (US); Michael X. Govea, Castaic, CA (US); Matthew Lee McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 134 days.

This patent is subject to a terminal disclaimer.

(21) Appl. No.: 17/890,188

(22) Filed: Aug. 17, 2022

(65) Prior Publication Data

US 2022/0401745 A1 Dec. 22, 2022

Related U.S. Application Data

(63) Continuation of application No. 16/678,918, filed on Nov. 8, 2019, now Pat. No. 11,426,595.

(Continued)

(51) Int. Cl.
*A61N 1/375* (2006.01)
*A61N 1/36* (2006.01)

(52) U.S. Cl.
CPC ......... *A61N 1/3752* (2013.01); *A61N 1/3756* (2013.01); *A61N 1/3606* (2013.01); *A61N 1/37514* (2017.08)

(58) Field of Classification Search
None
See application file for complete search history.

(56) References Cited

U.S. PATENT DOCUMENTS

| 4,920,979 A | 5/1990 | Bullara |
| 5,076,270 A | 12/1991 | Stutz, Jr. |

(Continued)

FOREIGN PATENT DOCUMENTS

| EP | 30204501 A1 | 5/2016 |
| WO | 02/091935 | 11/2002 |

(Continued)

OTHER PUBLICATIONS

U.S. Appl. No. 18/232,649, filed Aug. 10, 2023.
(Continued)

*Primary Examiner* — Erica S Lee
(74) *Attorney, Agent, or Firm* — Branch Partners PLLC; Bruce E. Black

(57) ABSTRACT

An adapter to add optical stimulation to a stimulation system includes an adapter body and a connector disposed on the distal end of the adapter body. The connector includes a connector body defining a port and a connector lumen; connector contacts disposed in the connector body and arranged along the connector lumen; and a light source disposed in the connector body. The adapter also includes terminals disposed along the proximal end of the adapter body and conductors extending along the adapter body and electrically coupling the connector contacts and the light source to the terminals. The adapter may be used with an optical stylet that fits into a stimulation lead which is, in turn, coupled to the connector of the adapter. Alternatively, the adapter can include a fiber optic coupled to the light source and configured to extend into the stimulation lead.

20 Claims, 9 Drawing Sheets

Related U.S. Application Data

(60) Provisional application No. 62/768,610, filed on Nov. 16, 2018.

(56) References Cited

U.S. PATENT DOCUMENTS

| | | |
|---|---|---|
| 5,437,193 A | 8/1995 | Schleitweiler et al. |
| 5,445,608 A | 8/1995 | Chen et al. |
| 5,556,421 A | 9/1996 | Prutchi et al. |
| 5,824,027 A | 10/1998 | Hoffer et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,366,719 B1 | 4/2002 | Heath et al. |
| 6,391,985 B1 | 5/2002 | Goode et al. |
| 6,442,435 B2 | 8/2002 | King et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,252,677 B2 | 8/2007 | Burwell et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,803,021 B1 | 9/2010 | Brase |
| 7,809,446 B2 | 10/2010 | Meadows |
| 7,946,980 B2 | 5/2011 | Reddy et al. |
| 7,949,395 B2 | 5/2011 | Kuzma |
| 7,949,409 B2 | 5/2011 | Bly et al. |
| 7,974,706 B2 | 7/2011 | Moffitt et al. |
| 8,086,322 B2 | 12/2011 | Schouenborg |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,311,647 B2 | 11/2012 | Bly |
| 8,326,433 B2 | 12/2012 | Blum et al. |
| 8,340,785 B2 | 12/2012 | Bonde et al. |
| 8,364,278 B2 | 1/2013 | Pianca et al. |
| 8,386,054 B2 | 2/2013 | North |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,525,027 B2 | 9/2013 | Lindner et al. |
| 8,571,665 B2 | 10/2013 | Moffitt et al. |
| 8,600,509 B2 | 12/2013 | McDonald et al. |
| 8,675,945 B2 | 3/2014 | Barnhorst et al. |
| 8,682,439 B2 | 3/2014 | DeRohan et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,831,746 B2 | 9/2014 | Swanson |
| 8,849,632 B2 | 9/2014 | Sparks et al. |
| 8,868,211 B2 | 10/2014 | Durand et al. |
| 8,897,876 B2 | 11/2014 | Sundaramurthy et al. |
| 8,929,973 B1 | 1/2015 | Webb et al. |
| 8,936,630 B2 | 1/2015 | Denison et al. |
| 8,958,615 B2 | 2/2015 | Blum et al. |
| 9,238,132 B2 | 1/2016 | Barker |
| 9,409,032 B2 | 8/2016 | Brase et al. |
| 9,415,154 B2 | 8/2016 | Leven |
| 9,421,362 B2 | 8/2016 | Seeley |
| 9,440,066 B2 | 9/2016 | Black |
| 9,550,063 B2 | 1/2017 | Wolf, II |
| 9,604,068 B2 | 3/2017 | Malinowski |
| 9,643,010 B2 | 5/2017 | Ranu |
| 9,656,093 B2 | 5/2017 | Villarta et al. |
| 9,681,809 B2 | 6/2017 | Sharma et al. |
| 9,770,598 B2 | 9/2017 | Malinowski et al. |
| 9,931,511 B2 | 4/2018 | Kaula et al. |
| 10,307,602 B2 | 6/2019 | Leven |
| 10,335,607 B2 | 7/2019 | Orinski |
| 10,471,273 B2 | 11/2019 | Segev et al. |
| 10,814,140 B2 | 10/2020 | Zhang et al. |
| 2002/0156513 A1 | 10/2002 | Borkan |
| 2002/0161417 A1 | 10/2002 | Scribner |
| 2004/0098063 A1 | 5/2004 | Goetz |
| 2004/0147964 A1 | 7/2004 | Nolan et al. |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh, Jr. et al. |
| 2007/0053996 A1 | 3/2007 | Boyden et al. |
| 2007/0100398 A1 | 5/2007 | Sloan |
| 2007/0150036 A1 | 6/2007 | Anderson |
| 2007/0161919 A1 | 7/2007 | DiLorenzo |
| 2007/0244524 A1 | 10/2007 | Qu et al. |
| 2007/0244526 A1 | 10/2007 | Zaghetto et al. |
| 2008/0046053 A1 | 2/2008 | Wagner et al. |
| 2008/0077190 A1* | 3/2008 | Kane ............... A61N 1/3752 607/37 |
| 2008/0077198 A1 | 3/2008 | Webb et al. |
| 2008/0146890 A1 | 6/2008 | LeBoeuf et al. |
| 2008/0167701 A1 | 7/2008 | John et al. |
| 2008/0197300 A1 | 8/2008 | Kayser et al. |
| 2008/0243218 A1 | 10/2008 | Bottomley et al. |
| 2009/0054954 A1 | 2/2009 | Foley et al. |
| 2009/0054955 A1 | 2/2009 | Kopell et al. |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0196471 A1 | 8/2009 | Goetz et al. |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2009/0299447 A1 | 12/2009 | Jensen et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0105997 A1 | 4/2010 | Ecker et al. |
| 2010/0114190 A1 | 5/2010 | Bendett et al. |
| 2010/0174329 A1 | 7/2010 | Dadd et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022100 A1 | 1/2011 | Brase et al. |
| 2011/0029055 A1 | 2/2011 | Tidemand |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0106208 A1 | 5/2011 | Faltys et al. |
| 2011/0112591 A1 | 5/2011 | Seymour et al. |
| 2011/0125077 A1 | 5/2011 | Denison et al. |
| 2011/0125078 A1 | 5/2011 | Denison et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0172725 A1 | 7/2011 | Wells et al. |
| 2011/0238129 A1 | 9/2011 | Moffitt et al. |
| 2011/0295331 A1 | 12/2011 | Wells et al. |

(56) References Cited

U.S. PATENT DOCUMENTS

| | | |
|---|---|---|
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1 | 4/2013 | Oki et al. |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0074182 A1 | 3/2014 | Wolf, II |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005680 A1 | 1/2015 | Lipani |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1 | 2/2015 | Goldman et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1* | 10/2015 | Nielsen ............... G02B 6/0008 607/3 |
| 2015/0321012 A1* | 11/2015 | Cinbis ............... A61N 1/36514 607/62 |
| 2015/0360031 A1 | 12/2015 | Bornzin et al. |
| 2015/0375006 A1 | 12/2015 | Denison et al. |
| 2016/0030749 A1 | 2/2016 | Carcieri et al. |
| 2016/0045740 A1 | 2/2016 | Rezai et al. |
| 2016/0067519 A1 | 3/2016 | Tranberg et al. |
| 2016/0082251 A1 | 3/2016 | Moffitt et al. |
| 2016/0082253 A1 | 3/2016 | Moffitt et al. |
| 2016/0151639 A1 | 6/2016 | Scharf et al. |
| 2016/0228692 A1 | 8/2016 | Steinke et al. |
| 2016/0250474 A1 | 9/2016 | Stack et al. |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0331994 A1 | 11/2016 | Smith et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0000419 A1 | 1/2017 | Schouenborg |
| 2017/0061627 A1 | 3/2017 | Bokil |
| 2017/0095670 A1 | 4/2017 | Ghaffari et al. |
| 2017/0100580 A1 | 4/2017 | Olson |
| 2017/0136254 A1 | 5/2017 | Simon et al. |
| 2017/0143985 A1 | 5/2017 | Degenaar et al. |
| 2017/0172446 A1 | 6/2017 | Kuzum et al. |
| 2017/0182191 A1 | 6/2017 | Towne et al. |
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0229042 A1 | 8/2018 | Kaula et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0326219 A1* | 11/2018 | Wolf, II ............... A61N 1/3758 |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0003898 A1 | 1/2019 | Dehkhoda et al. |
| 2019/0201709 A1 | 7/2019 | Tischendorf et al. |
| 2019/0209834 A1 | 7/2019 | Zhang et al. |
| 2019/0209849 A1 | 7/2019 | Hershey et al. |
| 2020/0001096 A1 | 1/2020 | Zhang et al. |
| 2020/0094047 A1 | 3/2020 | Govea et al. |
| 2020/0155854 A1 | 5/2020 | Leven et al. |
| 2020/0271796 A1 | 8/2020 | Tahon et al. |
| 2020/0323589 A1 | 10/2020 | Varol |
| 2020/0376262 A1 | 12/2020 | Clark et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |
| 2022/0054226 A1 | 2/2022 | Gregg, II et al. |
| 2022/0072329 A1 | 3/2022 | Howard |
| 2022/0323781 A1 | 10/2022 | Subramanian et al. |

FOREIGN PATENT DOCUMENTS

| | | |
|---|---|---|
| WO | 2010029297 | 3/2010 |
| WO | 2011/031131 | 3/2011 |
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |
| WO | 2021141163 | 7/2021 |

OTHER PUBLICATIONS

U.S. Appl. No. 18/232,621, filed Aug. 10, 2023.

Weiran Cao, Jian Li, Hongzheng Chen, Jiangeng Xue, "Transparent electrodes for organic optoelectronic devices: a review," J. Photon. Energy 4(1) 040990 (Oct. 30, 2014) https://doi.org/10.1117/1.JPE.4.040990.

Lee KT, Park DH, Baac HW, Han S. Graphene- and Carbon-Nanotube-Based Transparent Electrodes for Semitransparent Solar

(56) References Cited

OTHER PUBLICATIONS

Cells. Materials (Basel). Aug. 22, 2018;11(9):1503. doi: 10.3390/ma11091503. PMID: 30135379; PMCID: PMC6165141.
R G Wilson, "Ball-lens coupling efficiency for laser-diode to single-mode fiber: comparison of independent studies by distinct methods," Applied Optics May 20, 1998, 37 (15): 3201-5.
Official Communication for U.S. Appl. No. 16/678,918 mailed Oct. 27, 2021.
Official Communication for U.S. Appl. No. 16/678,918 mailed Feb. 9, 2022.
Official Communication for U.S. Appl. No. 16/678,918 mailed Jun. 8, 2022.
Baxter, G.D. et al., Effects of Low Intensity Infrared Laser Irradiation Upon Conduction in the Human Median Nerve In Vivo, Experimental Physiology (1994) 79, 227-234.
Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.
Kono, Toru et al., Cord Dorsum Potentials Suppressed by Low Power Laser Irradiation on a Peripheral Nerve in the Cat, Journal of Clinical Laser Medicine & Surgery (1993) 11:3, 115-118.
Snyder-Mackler, Lynn et al., Effect of Helium-Neon Laser Irradiation on Peripheral Sensory Nerve Latency, Phys. Ther. (1988), 68:223-225.
Darlot, Fannie et al., Near-infrared light is neuroprotective in a monkey model of Parkinson's disease (2006), 30 pages.
Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/S0896-6273(00)80955-1.
Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).
Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.
Use of NAD(P)H and flavoprotein autofluorescence transients to probe neuron and astrocyte responses to synaptic activation. Shuttleworth 2010 Neurochemestry international.
Vallejo, Ricardo, Kerry Bradley, and Leonardo Kapural. "Spinal cord stimulation in chronic pain: Mode of action." Spine 42 (2017): S53-S60.
Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.
International Search Report and Written Opinion for PCT Application No. PCT/US2019/060608 mailed Feb. 6, 2020.

* cited by examiner

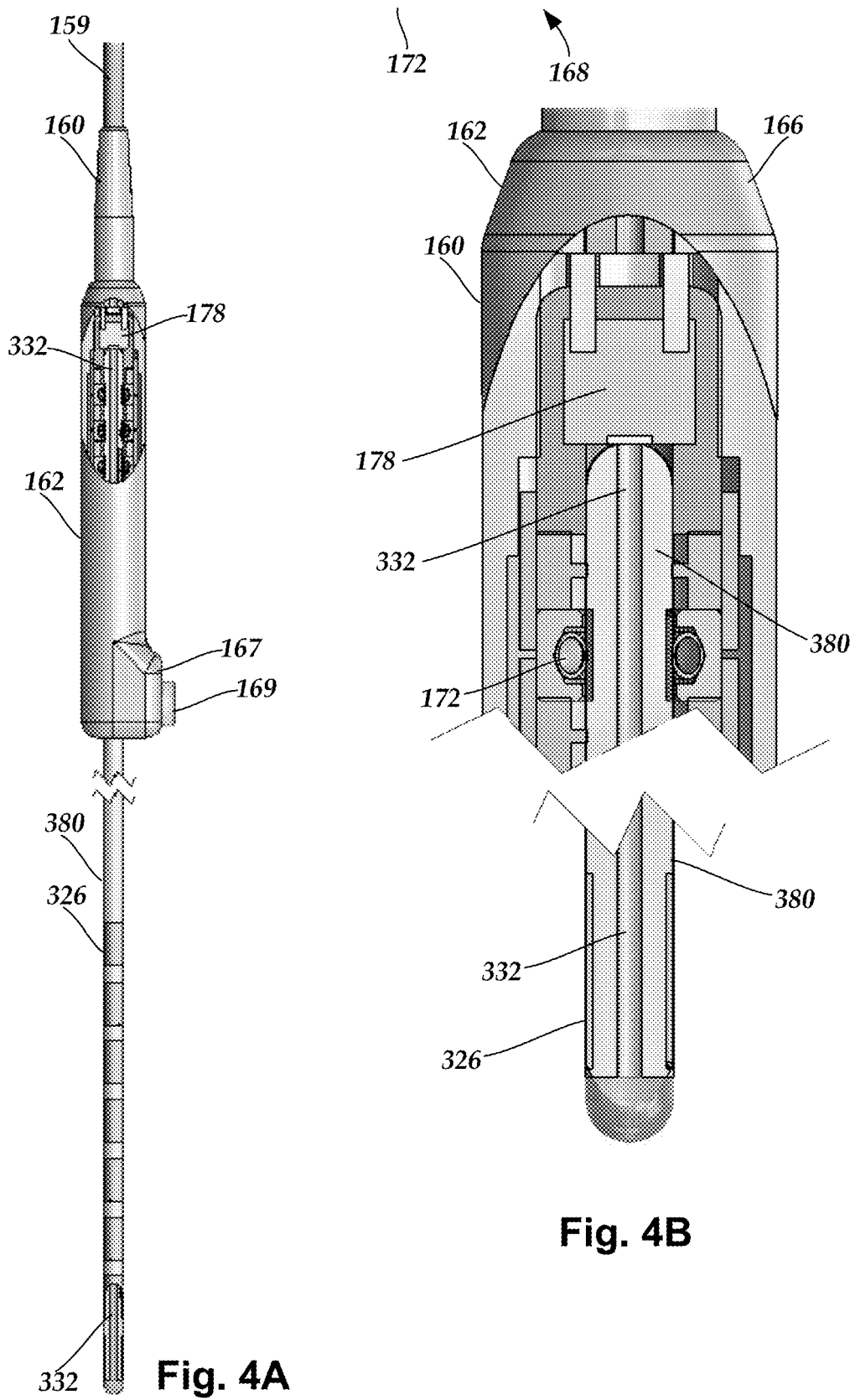

OPTICAL STIMULATION SYSTEM WITH ON-DEMAND MONITORING AND METHODS OF MAKING AND USING

CROSS-REFERENCE TO RELATED APPLICATIONS

This application is a continuation of U.S. patent application Ser. No. 16/678,918, filed Nov. 8, 2019, which issued as U.S. Pat. No. 11,426,595, which claims the benefit under 35 U.S.C. § 119(e) of U.S. Provisional Patent Application Ser. No. 62/768,610, filed Nov. 16, 2018, both of which are incorporated herein by reference.

FIELD

The present disclosure is directed to the area of implantable electrical/optical stimulation systems and methods of making and using the systems. The present disclosure is also directed to implantable electrical stimulation systems that include an arrangement for also providing optical stimulation using a connector or adapter that produces light.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Optical stimulation can also provide therapeutic benefits in a variety of diseases and disorders by itself or in combination with electrical stimulation. An optical stimulation system may include a stimulator with one or more light sources and, often, one or more optical fibers to carry the light to the desired stimulation site.

BRIEF SUMMARY

In one aspect, an adapter for a stimulation system includes an adapter body having a distal end and a proximal end and a connector disposed on the distal end of the adapter body. The connector includes a connector body defining a port and a connector lumen extending from the port for receiving a proximal end of a stimulation lead; connector contacts disposed in the connector body and arranged along the connector lumen; and a light source disposed in the connector body. The adapter also includes terminals disposed along the proximal end of the adapter body and conductors extending along the adapter body and electrically coupling the connector contacts and the light source to the terminals.

In at least some aspects, the light source is disposed at a proximal end of the connector lumen. In at least some aspects, the adapter further includes a fiber optic extending from the light source to or through the connector lumen. In at least some aspects, the connector body defines a fiber optic port through which the fiber optic extends. In at least some aspects, the fiber optic is configured to be slidably movable through the fiber optic port. In at least some aspects, the fiber optic extends through the connector lumen and is configured for a portion of the fiber optic to be received within a stimulation lead.

In at least some embodiments, the fiber optic comprises a core and a cladding disposed around the core. In at least some embodiments, the cladding comprises at least one emission region, wherein an index of refraction of the emission region is greater than an index of refraction of the core. In at least some embodiments, the at least one emission region comprises at least one directional emission region, wherein the directional emission region extends around no more than 75% of a circumference of the fiber optic.

In another aspect, a kit for providing optical stimulation includes any of the adapters described above and an optical stylet configured to receive and transmit light from the light source when a portion of the optical stylet is inserted into the connector of the adapter.

In at least some aspects, the optical stylet includes a core and a cladding disposed around the core. In at least some aspects, the cladding includes at least one emission region, where an index of refraction of the emission region is greater than an index of refraction of the core. In at least some aspects, the at least one emission region includes at least one directional emission region, where the directional emission region extends around no more than 75% of a circumference of the optical stylet.

In at least some aspects, the kit further includes an electrical stimulation lead having a lead body having a distal end portion and a proximal end portion and defining a lumen configured for receiving the optical stylet, wherein the proximal end portion is configured for insertion through the port of the connector and into the connector lumen of the connector; electrodes disposed along the distal end portion of the lead body; terminals disposed along the proximal end portion of the lead body; and conductors extending along the lead body and electrically coupling the electrodes to the terminals. In at least some aspects, the optical stylet is removably insertable into the lumen of the electrical stimulation lead. In at least some aspects, the optical stylet is permanently disposed in the lumen of the electrical stimulation lead.

Yet another aspect is a system for electrical/optical stimulation that includes any of the kits described above, as was as an electrical stimulation lead having a lead body having a distal end portion and a proximal end portion and defining a lumen configured for receiving the optical stylet, where the proximal end portion is configured for insertion through the port of the connector and into the connector lumen of the connector; electrodes disposed along the distal end portion of the lead body; terminals disposed along the proximal end portion of the lead body; and conductors extending along the lead body and electrically coupling the electrodes to the terminals. The system also includes a control module having a control module connector defining a port and a connector lumen extending from the port for receiving a proximal end of the adapter, the control module connector including connector contacts disposed in the connector body and arranged along the connector lumen; a housing coupled to the control module connector; and an electronic subassembly disposed in the housing and electrically coupled to the connector contacts of the control module connector.

In a further aspect, a kit for providing optical stimulation includes any of the adapters described above that includes a fiber optic, as well as an electrical stimulation lead having a lead body having a distal end portion and a proximal end portion and defining a lumen configured for receiving the fiber optic of the adapter, where the proximal end portion is configured for insertion through the port of the connector and into the connector lumen of the connector; electrodes disposed along the distal end portion of the lead body; terminals disposed along the proximal end portion of the lead body; and conductors extending along the lead body and electrically coupling the electrodes to the terminals.

In at least some aspects, the kit further includes an optical stylet configured to receive and transmit light from the light source when a portion of the optical stylet is inserted into the connector of the adapter.

Another aspect is a system for electrical/optical stimulation that includes any of the kits described above that have an electrical stimulation lead and an adapter with an fiber optic. The system also includes a control module having a control module connector defining a port and a connector lumen extending from the port for receiving a proximal end of the adapter, the control module connector including connector contacts disposed in the connector body and arranged along the connector lumen; a housing coupled to the control module connector; and an electronic subassembly disposed in the housing and electrically coupled to the connector contacts of the control module connector.

A further aspect is a method of assembling an optical stimulation system. The method includes providing any of the adapters or kits described above; electrically coupling the adapter to a control module; and inserting a fiber optic or an optical stylet optically coupled to the fiber optic into a lead.

Another aspect is a method of optically stimulating patient tissue. The method includes providing any of the adapters or kits described above; electrically coupling the adapter to a control module; inserting the fiber optic or an optical stylet optically coupled to the fiber optic into a lead; implanting the lead into the patient tissue; generating optical stimulation from the light source using the control module; and delivering the optical stimulation along i) the fiber optic or ii) the fiber optic and optical stylet to the patient tissue.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4A is a schematic side view, with cut-away regions, of portion of one embodiment of an adapter, optical stylet, and lead coupled together;

FIG. 4B is a schematic magnified view of the cut-away regions of FIG. 4A;

DETAILED DESCRIPTION

The present disclosure is directed to the area of implantable electrical/optical stimulation systems and methods of making and using the systems. The present disclosure is also directed to implantable electrical stimulation systems that include an arrangement for also providing optical stimulation using a connector or adapter that produces light.

The stimulation systems described herein can produce both optical and electrical stimulation. In at least some of these embodiments, the optical stimulation can be provided through a modification of an electrical stimulation system. Optical stimulation may include, but is not necessarily limited to, stimulation resulting from response to particular wavelengths or wavelength ranges of light or from thermal effects generated using light or any combination thereof.

Figure 1A:
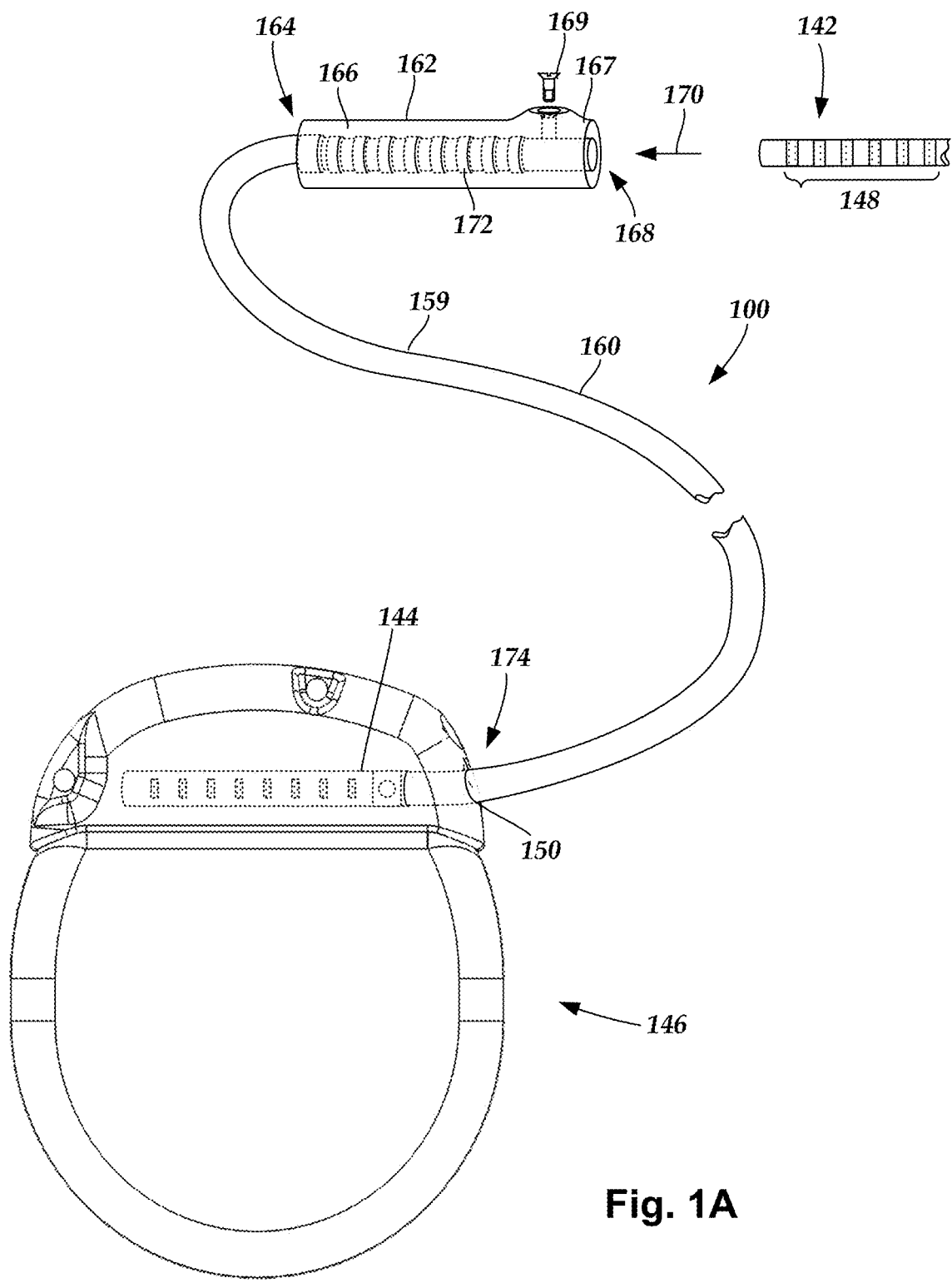
FIG. 1A is a schematic side view of one embodiment of an arrangement including a control module, an adapter, and a portion of an electrical stimulation lead.

FIG. 1A is a schematic side view of a portion of an embodiment of an electrical/optical stimulation system 100. The optical stimulation system 100 includes an adapter 160 (which optionally may also function as a lead extension, as illustrated in FIG. 1A) that is configured to couple one or more proximal ends 142 of a lead to the control module 146. In FIG. 1A, the adapter 160 is shown coupled to a single port 150 defined in the control module connector 144. Additionally, the adapter 160 is shown configured to couple to a single proximal end 142 of a lead (for example, the lead 180 of FIG. 1C).

Figure 2:
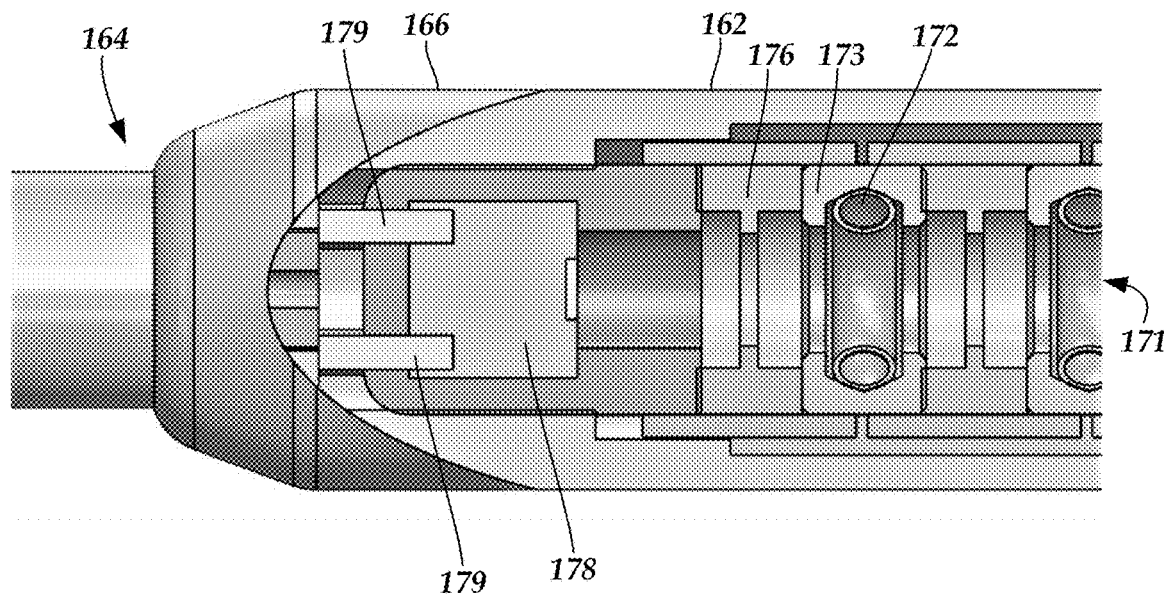
FIG. 2 is a schematic side view, with a cut-away region, of a portion of the adapter of FIG. 1A.

The adapter 160 includes a connector 162 and at least one adapter body 159 extending from the connector. In FIG. 1A, the adapter connector 162 is shown disposed at a distal end 164 of the adapter 160. The adapter connector 162 includes a connector housing 166. The connector housing 166 defines at least one port 168 into which terminals 148 of the proximal end 142 of the lead can be inserted, as shown by directional arrow 170. The connector housing 166 also includes a plurality of connector contacts, such as connector contact 172. When the proximal end 142 is inserted into the port 168, the connector contacts 172 disposed in the connector housing 166 can be aligned with the terminals 148 for electrical coupling. In addition, as illustrated in FIG. 2, the connector 162 may also include a light source 178.

In at least some embodiments, the adapter connector 162 further includes a retention block 167 to fasten the corresponding lead body (or a retention ring on the lead body) of the lead or lead extension to the connector 162 when the lead body is inserted into the connector assembly and prevent undesired detachment of the lead body from the connector assembly or misalignment of the terminals on the lead body with the connector contacts. For example, the retention block 167 may include an aperture through which a fastener 169 (e.g., a set screw, pin, or the like) may be inserted and secured against an inserted lead body. Other types of retention blocks or retention assemblies can be used including, but not limited to, those described in U.S. Pat. No. 9,440,066; U.S. patent application Ser. Nos. 15/627,016 and 15/641,688; and U.S. Provisional Patent Application Ser. No. 62/464,710, all of which are incorporated herein by reference.

In at least some embodiments, the proximal end 174 of the adapter 160 is similarly configured as a proximal end 142 of a lead with terminals (such as terminals 148 in FIG. 1B) disposed along the proximal end of the adapter body 159. The adapter 160 includes conductors (not shown), such as electrically conductive wires or cables, that electrically couple the connector contacts 172 to the terminals (not shown) on the proximal end 174 of the adapter 160. In at least some embodiments (as shown in FIG. 1A), the proximal end 174 of the adapter 160 is configured for insertion into a port 150 of a control module connector 144 or other connector. In other embodiments, the proximal end may be permanently attached to the control module 146.

Figure 1B:
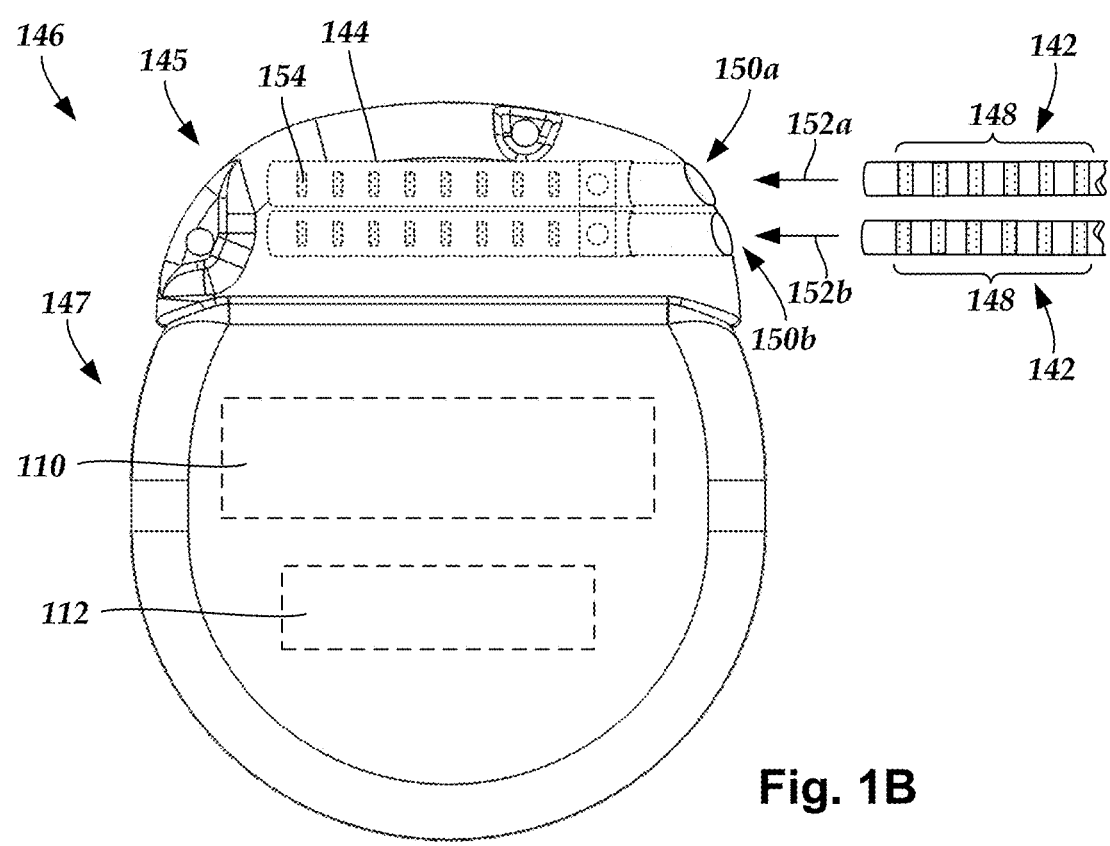
FIG. 1B is a schematic side view of one embodiment of a control module configured to electrically couple to a lead or lead extension.

FIG. 1B is a schematic side view of one embodiment of proximal ends 142 of one or more adapters or leads (for example, adapter 160 of FIG. 1A or lead 180 of FIG. 1C) coupling to a control module 146 (or other device) through one or more control module connectors 144. The one or more proximal ends 142 include terminals 148 (such as the terminals of adapter 160).

The control module connector 144 defines at least one port 150a, 150b into which a proximal end 142 can be inserted, as shown by directional arrows 152a and 152b. The control module 146 (or other device) can define any suitable number of ports including, for example, one, two, three, four, five, six, seven, eight, or more ports.

The control module connector 144 also includes a plurality of connector contacts, such as connector contact 154, disposed within each port 150a and 150b. When the proximal end 142 is inserted into the ports 150a and 150b, the connector contacts 154 can be aligned with a plurality of terminals 148 disposed along the proximal end(s) 142. Examples of connectors in control modules are found in, for example, U.S. Pat. Nos. 7,244,150 and 8,224,450, which are incorporated by reference, as well as other references listed herein.

In at least some embodiments, the control module 146 includes a connector housing 145 and a sealed electronics housing 147. In at least some embodiments, an electronic subassembly 110 and an optional power source 112 are disposed in the electronics housing 147. Other embodiments of a control module 146 may have more or fewer components.

Figure 1C:
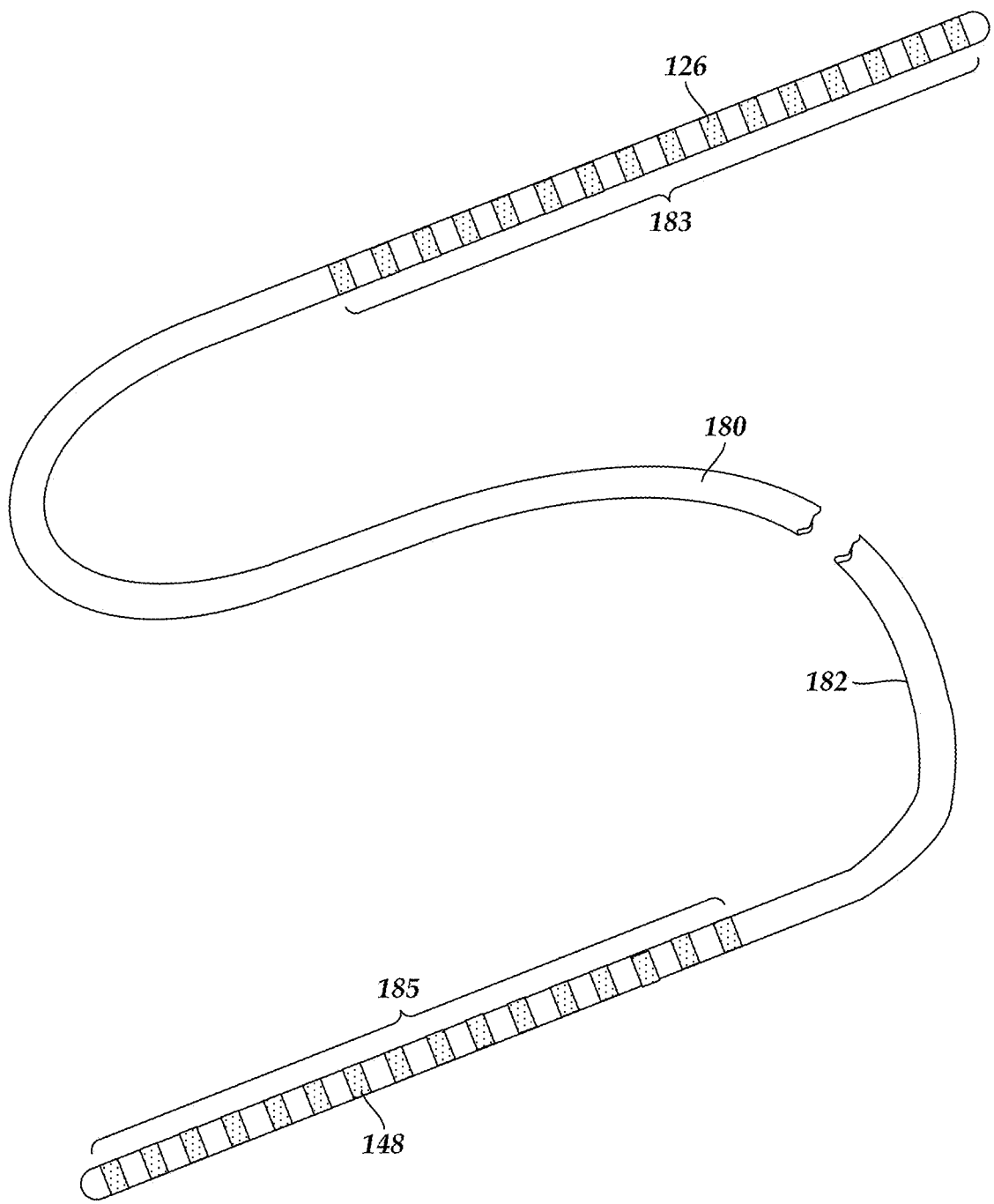
FIG. 1C is a schematic side view of one embodiment of an electrical stimulation lead.

FIG. 1C illustrates schematically one embodiment of an electrical stimulation lead 180 coupleable to the control module 146 or the adapter 160. The lead 180 includes one or more lead bodies 182, an array 183 of electrodes 126, and an array 185 of terminals 148 disposed along the one or more lead bodies 182. In at least some embodiments, the lead is isodiametric along a longitudinal length of the lead body 182. Conductors (not shown), such as electrically conductive wires, cables, or the like, extend from the terminals 148 to the electrodes 126. Typically, one or more electrodes 126 are electrically coupled to each terminal 148. In at least some embodiments, each terminal 148 is only connected to one electrode 126.

The lead 180 can be coupled to the control module 146 in any suitable manner. In at least some embodiments, the lead 180 couples directly to the control module 146. In at least some other embodiments, the lead 180 couples to the control module 146 via one or more intermediate devices, such as the adapter 160. For example, in at least some embodiments one or more adapters 160 or lead extensions can be disposed between the lead 180 and the control module 146 to extend the distance between the lead 180 and the control module 146. Other intermediate devices may be used in addition to, or in lieu of, one or more lead extensions including, for example, a splitter or the like or any combination thereof. It will be understood that, in the case where the electrical stimulation system 100 includes multiple elongated devices disposed between the lead 180 and the control module 146, the intermediate devices may be configured into any suitable arrangement.

The electrical stimulation system or components of the electrical stimulation system, including one or more of the leads 180 and the control module 146, are typically implanted into the body of a patient. The electrical stimulation system can be used for a variety of applications including, but not limited to, brain stimulation, neural stimulation, spinal cord stimulation, muscle stimulation, and the like.

The electrodes 126, terminals 148, and conductive contacts 154, 172 can be formed using any conductive, biocompatible material. Examples of suitable materials include metals, alloys, conductive polymers, conductive carbon, and the like, as well as combinations thereof. In at least some embodiments, one or more of the electrodes 126 or terminals 148 are formed from one or more of: platinum, platinum iridium, palladium, palladium rhodium, or titanium. The number of electrodes 126 in each array 183, the number of terminals 148 in each array 185, and the number of conductor contacts 154, 172 in a connector 144,162 may vary. For example, there can be two, four, six, eight, ten, twelve, fourteen, sixteen, or more electrodes 126, terminals 148, or conductor contacts 144, 162. As will be recognized, other numbers of electrodes 126, terminals 148, or conductor contacts 154, 172 may also be used.

The lead body 182 and adapter body 159 can be made of any suitable materials. For example, the lead body 182 and adapter body 159 can be made of non-conductive materials, such as silicone or polyurethane, forming a jacket or other conductor guide structures through which the conductors extend.

Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316;

2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

FIG. 2 illustrates a portion of one embodiment of the adapter connector 162 partially cut-away to illustrate components within the adapter connector. In this embodiment, the adapter connector 162 includes a connector housing 166, a connector lumen 171 (which extends from the connector port 168—FIG. 1A), connector contacts 172 arranged along the connector lumen, contact housings 173 to hold the connector contacts, spacers 176 disposed between the connector contacts, and a light source 178 disposed at the proximal end of the connector lumen.

The connector housing 166 can be made of any suitable material or materials including, but not limited to, silicone, polyurethane, other plastic, metal, or ceramic or any combination thereof. The connector contacts 172 may take the form of conductive spring contacts or any other suitable contact arrangement. Examples of connector contacts include, but are not limited to, canted coil contacts available from Bal Seal Engineering, Inc. (Foothill Ranch, CA) and contacts described in U.S. Pat. Nos. 7,803,021; 8,682,439; 8,897,876; 9,409,032; 9,604,068; 9,656,093; and 9,770,598; U.S. Patent Application Publications Nos. 2011/0022100; 2016/0228692; and 2016/0296745; U.S. patent application Ser. Nos. 15/627,016 and 15/656,612; and U.S. Provisional Patent Application Ser. No. 62/483,141, all of which are incorporated herein by reference. The contact housing 173 (which may be absent in some embodiments) provide a seat for the contact 172 and may be formed of conductive or non-conductive material or any combination thereof. As indicated above, conductors are coupled to the contacts 172 and extend through the adapter 160 to terminals on the adapter. The conductors may be attached directly to the contacts 172 or may be attached to conductive contact housings 173 which are, in turn, electrically coupled to the contacts 172 or may be coupled to the contacts using any other suitable coupling arrangement.

The spacers 176 can be made of any suitable non-conductive material including, but not limited to, silicone, polyurethane, or the like. The spacers 176 electrically isolate the contacts 172 from each other. In at least some embodiments, the spacers 176 may be flexible and may provide at least a partial seal to reduce, or even eliminate, seepage of fluid into the connector from the environment external to the connector.

The light source 178 can be, for example, a laser diode, a light emitting diode (LED), an organic light emitting diode (OLED), a lamp, or any other suitable light source. In at least some embodiments, the light source 178 may act as an end stop to insertion of the lead into the adapter connector 162. In other embodiments, there may be another component that acts as an end stop to halt insertion of the lead into the adapter connector 162 prior to engagement of the lead with the light source 178.

The light source 178 is positioned to produce light that can then be transmitted along the lead, as described below. The light source 178 is electrically coupled to the terminals of the adapter 160 by conductors 179. In at least some embodiments, conductors 179 are coupled to the light source 178 to provide power to the light source. These conductors 179 are attached to terminals of the adapter 160 (for example, terminals 148 of FIG. 1B) that are inserted into the control module 146 to receive power from the control module for operating the light source 178. Alternatively, the connector 162 or other portion of the adapter may include a power source for the light source 178. In some embodiments, although the light source 178 is electrically coupled to the terminals of the adapter 160 by the conductors 179, there may also be one or more additional components, such as an electrical-to-optical signal converter, between the light source 178 and the terminals.

Figure 3A:
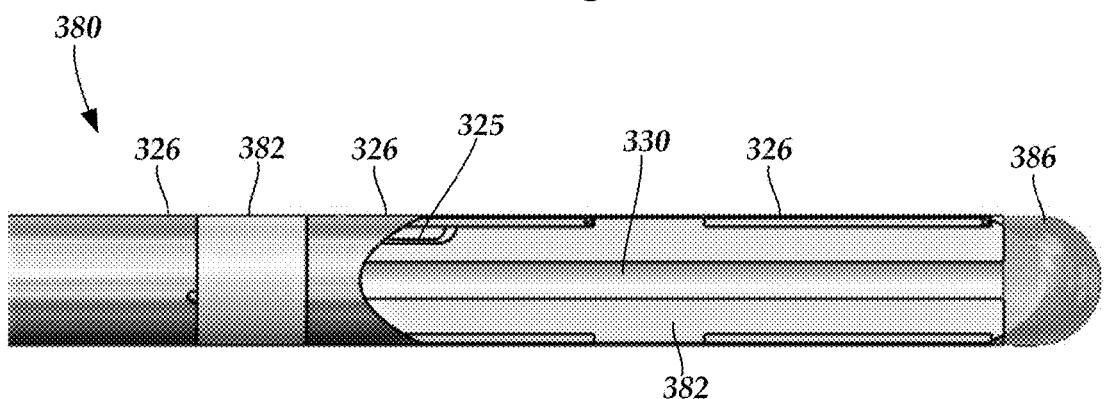
FIG. 3A is a schematic side view, with a cut-away region, of a portion of the electrical stimulation lead of FIG. 1C.

FIG. 3A illustrates a distal portion of one embodiment of a lead 380 partially cut-away to illustrate components within the lead. The lead includes a lead body 382, electrodes 326, and an optional light emission tip 386 which may be a lens, a diffuser, a transparent or translucent tip, or any combination thereof or any other suitable arrangement for emission of light. FIG. 3A includes a cut-away section to illustrate one of the conductors 325 and a central lumen 330.

Figure 3B:
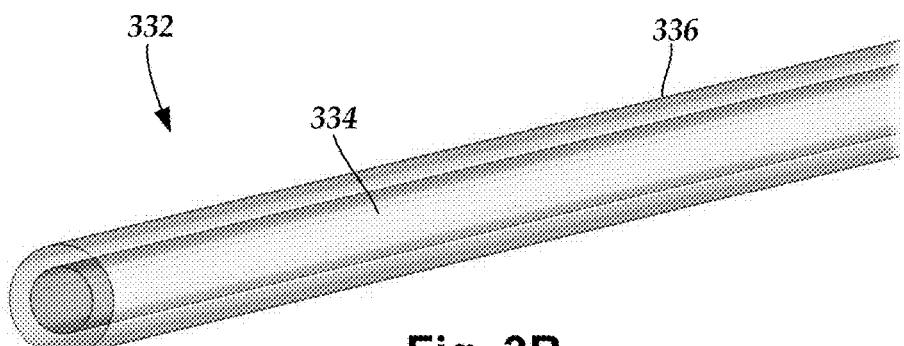
FIG. 3B is a schematic perspective view of a portion of one embodiment of an optical stylet.

FIG. 3B illustrates a portion of one embodiment of an optical stylet 332 that can be, for example, an optical fiber (or multiple optical fibers) with a core 334 and a cladding 336. The optical stylet 332 is configured for insertion in the central lumen 330 of the lead 380 and for carrying light from the light source 178 in the connector 162 along the lead 380 to the light emission tip 386 (or one or more other light emission regions along the lead, as described below) when the proximal end of the lead is inserted into the connector.

The terms "optical fiber" and "fiber optic" are used interchangeably herein and include light guides. The core of an optical fiber can be made of, for example, glass, polymer (such as silicone), or any other suitable material. The cladding can also be made of any suitable material including, but not limited to, polymers such as fluoropolymers.

In at least some embodiments, the optical stylet 332 can be used as both a steering or implantation stylet and as a conduit for light to provide optical stimulation of tissue. Thus, in at least some embodiments, the optical stylet 332 has multiple uses and purposes. Alternatively, in at least some embodiments, a separate steering or implantation stylet may be used for implantation of the lead and then replaced after implantation with the optical stylet 332.

FIGS. 4A and 4B illustrate the lead 380 with inserted optical stylet 332 coupled to the connector 162 of the adapter 160. FIG. 4B includes cutaway portions of the lead 380 and adapter 160 in order to view components within the lead and adapter. As illustrated, the proximal end of the optical stylet 332 is positioned to receive light from the light source 178 in the connector 162. In at least some embodiments, the optical stylet 332 is removable from the lead 380. In other embodiments, the optical stylet 332 is permanently disposed in the lead. For example, instead of a removable optical stylet, a permanently emplaced optical fiber traverses the longitudinal length of the lead. It will be recognized that, although the optical stylet 332 is disposed in the central lumen 330 of the lead 380 in the illustrated embodiment, in other embodiments, the optical stylet 332 (or an optical fiber or multiple optical fibers or stylets) can be disposed in a non-central lumen or other portion of the lead.

Figure 5A:
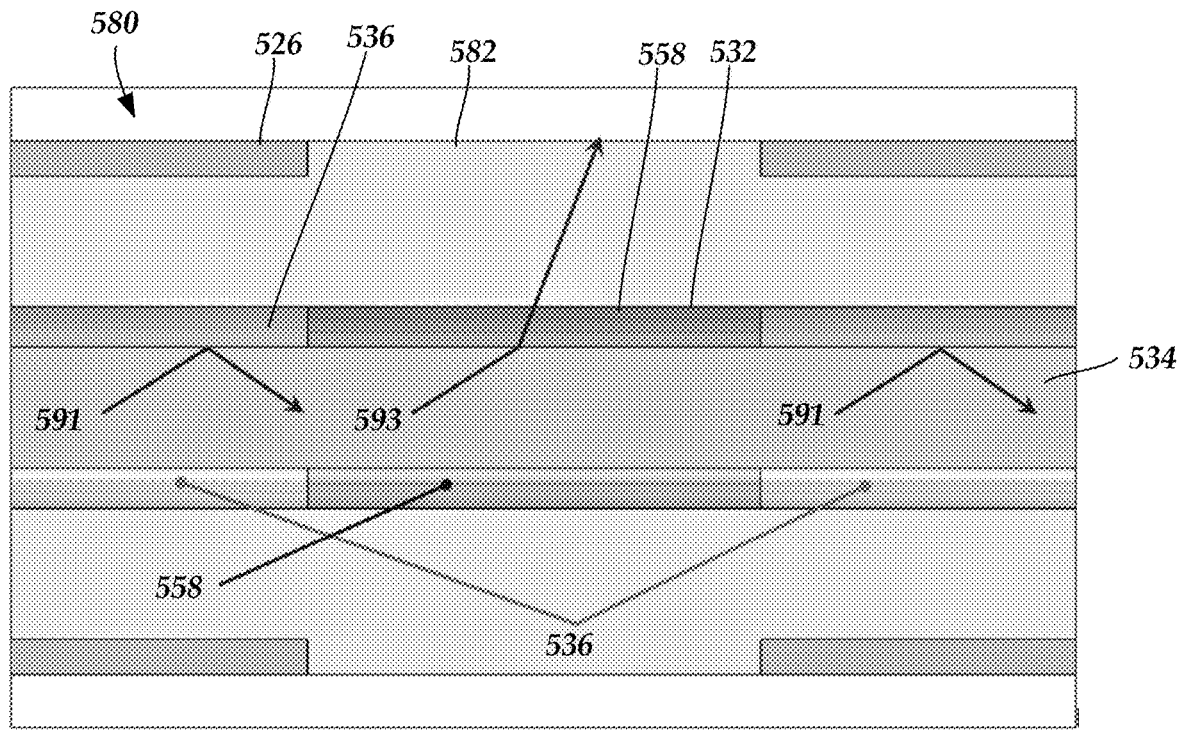
FIG. 5A is a schematic cross-sectional view of portions of one embodiment of a lead and optical stylet.
Figure 5B:
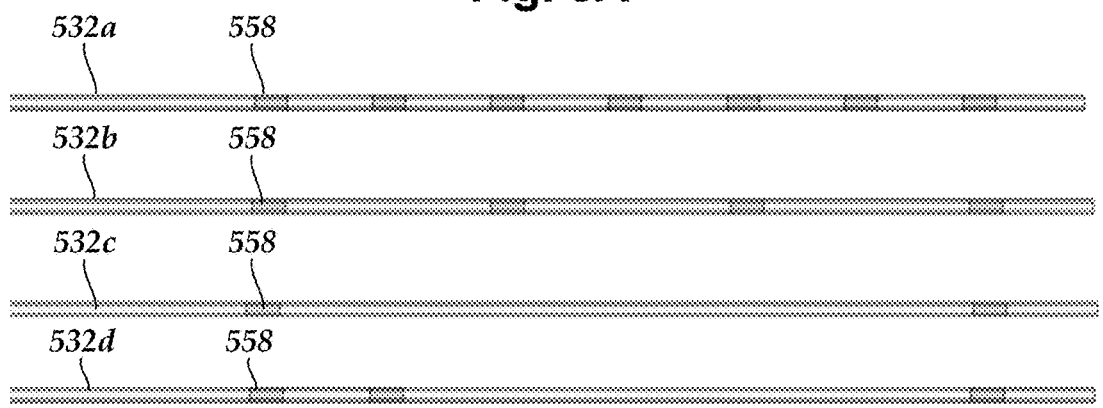
FIG. 5B presents side views of portions of embodiments of optical stylets with different arrangements of emission regions.
Figure 5C:
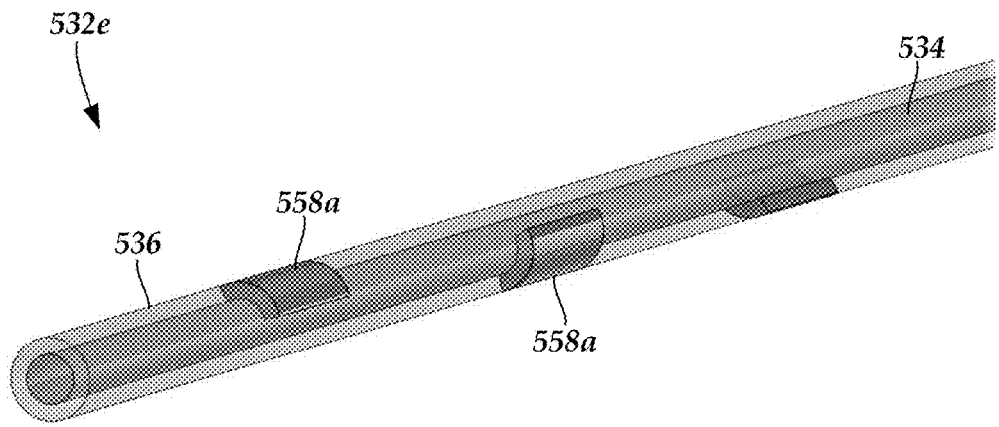
FIG. 5C is a schematic perspective view of a portion of one embodiment of an optical stylet with directional emission regions.

FIGS. 5A to 5C illustrate alternative optical stylets that are arranged to emit light at positions other than the distal end of the optical stylet. For example, these stylets may provide light emission out of the side of the lead, instead of, or in addition to, the end of the lead.

FIG. 5A illustrates a portion of a lead 580 with electrodes 526 and a lead body 582 (which may include, but is not limited to, a spacer between electrodes or a jacket for the lead). Within the lead 580 is an optical stylet 532 (or an optical fiber) that includes a core 534, a cladding 536, and light emission regions 558 formed in the cladding. In general, the cladding 536, except at the light emission regions 558, has an index of refraction, n, (for at least one or more wavelengths of light that are to be transmitted along the optical stylet 332) that is less than the index of refraction, $n_{core}$, of the core 534 ($n<n_{core}$). Light 591 transmitted along the core 534 will be reflected at the barrier between the core and cladding 536 if the angle of incidence, θ, is less than a critical angle defined as $\sin^{-1}(n/n_{core})$ where n is the index of refraction of the cladding and $n_{core}$ is the index of refraction of the core. Typically, light that is present at this portion of the optical stylet 532, which is relatively distant from the light source 178 (FIG. 2) and near the electrodes 526, has an angle of incidence less than or equal to the critical angle because light that did not meet this criterion will typically have already exited the optical stylet nearer the light source.

In FIGS. 5A to 5C, the cladding 536 of the optical stylet 532 (or optical fiber) is modified, removed, or replaced at one or more emission regions 558 along the optical stylet (or optical fiber). As illustrated in FIG. 5B, an optical stylet may have one, two, three, four, six, eight, ten, twelve, or more emission regions. In at least some embodiments, the optical stylet 532 and lead 580 may be arranged so that the emission regions 558 on the optical stylet 532 are aligned with spaces between the electrodes 526 when the optical stylet is disposed in the lead.

In at least some embodiments, the material of the emission regions 558 adjacent the core 534 is selected to have an index of refraction, n', that is greater than or equal to the index of refraction, $n_{core}$, of the core 534 ($n' \geq n_{core}$). This arrangement will typically result in most or all of the incident light 593 being transmitted through the emission region 558. Light incident on the emission regions 558 will leave the core 534 and be transmitted through the emission region 558 and out of the lead 380 (unless reflected by the electrodes 526 or lead body/tissue interface). In at least some embodiments, to limit the amount of light that is transmitted, the material of the emission regions 558 adjacent the core 534 is selected to have an index of refraction, n', that is greater than the index of refraction, n, of the cladding 532, but less than the index of refraction of the core 534, $n_{core}$ ($n<n', <n_{core}$).

Preferably, the lead body 582, at least in the portions of the lead where it may be desirable to transmit light out of the optical stylet 532, is made of material that is transparent or translucent to the light emitted from the optical stylet 532. In some embodiments, the lead body 582 may include a lens, diffuser, or other optical element at positions from which light can be emitted from the optical stylet 532. In some embodiments, the emission regions 558 may include a lens, diffuser, or other optical element.

FIG. 5B illustrates various arrangements of emission regions 558 on portions of different optical stylets 532a, 532b, 532c, 532d. The emission regions 558 can be spaced apart at regular intervals (optical stylets 532a, 532b, 532c) or different intervals (optical stylet 532d) or even at random or irregular intervals. Any suitable arrangement of emission regions can be used. The emission regions 558 in FIG. 5B are optionally cylindrical and wrap around the entire outer circumference of the optical stylet. An optical stylet may have any number of emission regions including, but not limited to, one, two, three, four, six, eight, ten, twelve, or more emission regions.

FIG. 5C illustrates a portion of one embodiment of an optical stylet 532e with one or more directional emission regions 558a where the directional emission region wraps around only a portion of the outer circumference of the optical stylet. For example, a directional emission region may wrap around only 10, 20, 30, 40, 50, 60, 70, 75, 80, or 90% of the outer circumference of the optical stylet 532. Light within the optical stylet 532e and incident on the directional emission regions 558a will be emitted, but light incident on the cladding adjacent the directional emission regions will remain in the optical stylet. The directional emission regions 558a can be used to limit the emission light to only a portion of the circumference of the optical stylet 532e (and also the lead), thereby providing a directionality to the light emission as opposed to a cylindrical emission region 558 where light is emitted around the entire circumference of the optical stylet. An optical stylet may have any number of directional emission regions including, but not limited to, one, two, three, four six, eight, ten, twelve, or more directional emission regions. In some embodiments, an optical stylet may have any combination of circumferential emission regions and directional emission regions.

Figure 6A:
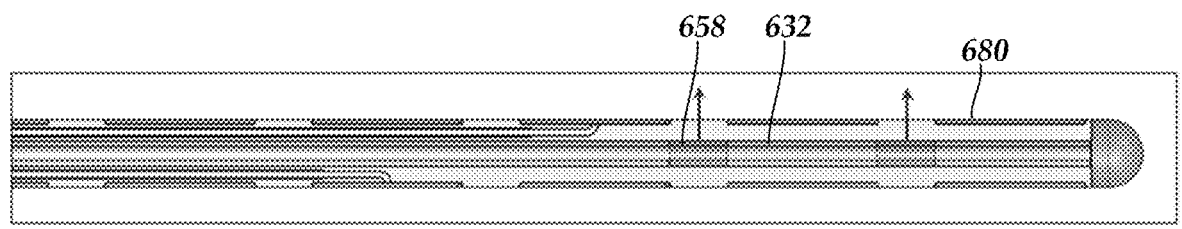
FIG. 6A is a schematic cross-sectional view of portions of one embodiment of a lead and optical stylet.
Figure 6B:
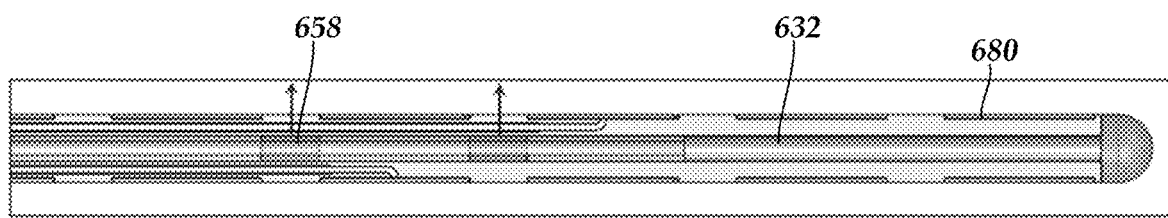
FIG. 6B is a schematic cross-sectional view of portions of the lead and optical stylet of FIG. 6A with the position of the optical stylet altered relative to the lead.

FIGS. 6A and 6B illustrate another feature of at least some embodiments of the optical stylet 632. In FIG. 6A, the optical stylet 632 is positioned in lead 680 so that the optical stylet extends to the distal end of the lead. In at least some embodiments, a proximal portion of the optical stylet can be removed or cut to adjust the position of the light emission regions 658 of the optical stylet. In FIG. 6B, a portion of the optical stylet 632 has been removed, as compared to FIG. 6A, so that the two light emission regions 658 are shifted proximally.

Figure 7:
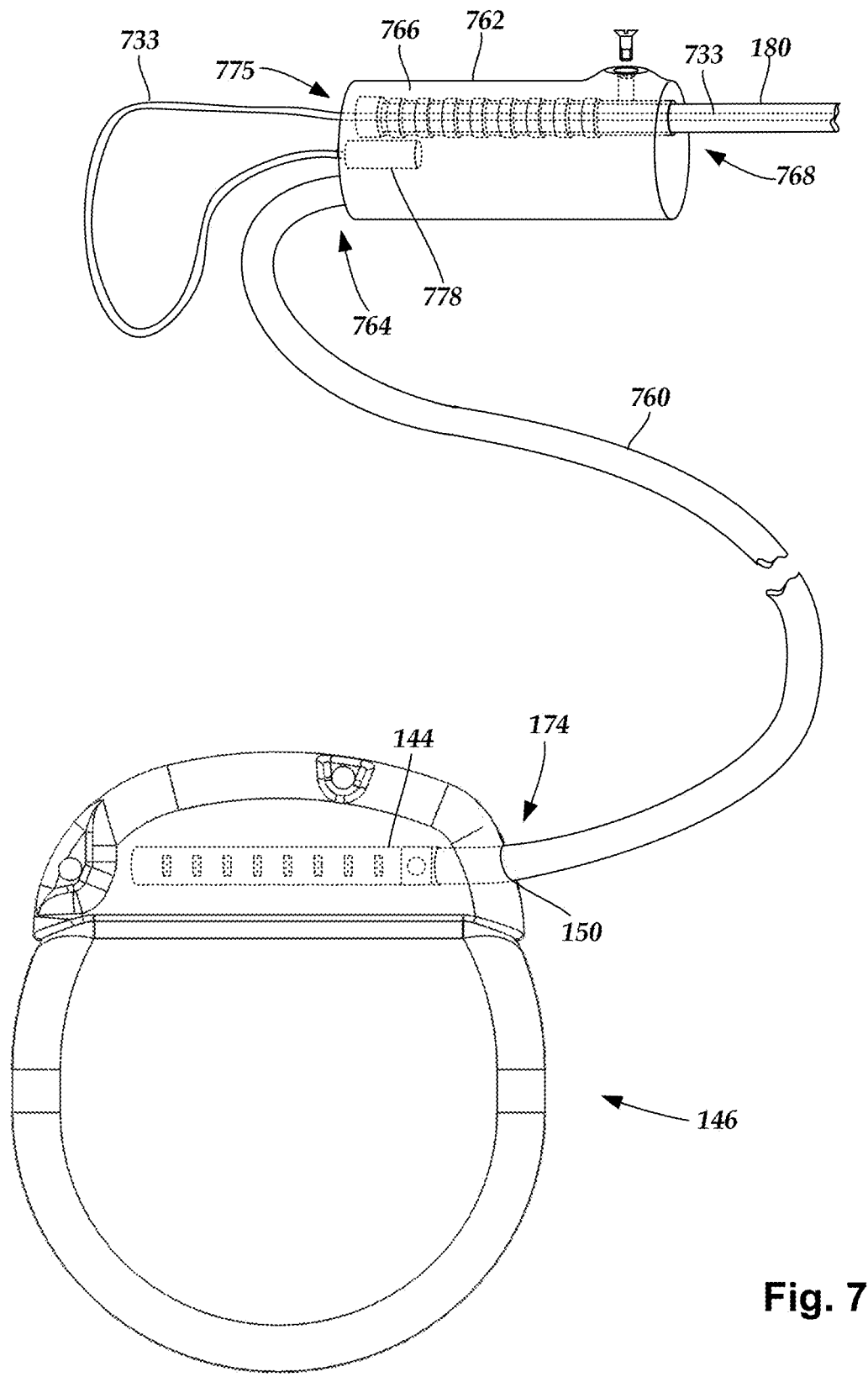
FIG. 7 is a schematic side view of another embodiment of an arrangement including a control module, an adapter, and a portion of an electrical stimulation lead;#

FIG. 7 illustrates another embodiment of an adapter 760 that includes a connector 762 is disposed on the distal end 764 of the adapter 760. The adapter 760 can have the same components, features, and options as the adapter 160 except as noted below. The adapter connector 762 includes a connector housing 766, at least one port 768 into which the proximal end of a lead 180 can be inserted, a connector lumen (similar to connector lumen 171 of FIG. 2) that extends from the connector port, and connector contacts 772 disposed along that connector lumen. When the proximal end of the lead 180 is inserted into the port 768, the connector contacts 772 disposed in the connector housing 766 can be aligned with the terminals of the lead for electrical coupling.

The connector 762 also includes a light source 778; however, unlike the light source 178 of FIG. 2, the light source 778 is not disposed along the connector lumen, but is offset from the connector lumen and connector contacts 772 and disposed in a different portion of the connector housing 766. The connector 762 includes a fiber optic 733 (or optical fiber) that receives light from the light source 778. In at least some embodiments, the fiber optic 733 is directly attached or coupled to the light source 778 to facilitate transfer of light from the light source to the fiber optic. In at least some embodiments, the fiber optic 733 then extends out of the connector housing 766, as illustrated in FIG. 7, and reenters the connector housing 766 through a port 775. The fiber optic 733 then extends along the connector lumen so that the fiber optic can be inserted into the proximal end of the lead 780 and can extend along the lead, as illustrated in FIG. 7, like the optical stylet 332, 532, 532'. Alternatively, instead of exiting the connector housing 766, the fiber optic 733 may extend within the connector housing 766 from the light source 778 into the connector lumen. The fiber optic 733 can include any of the features and options described above for the optical stylet 332, 532, 532' including, but not limited to, light emission regions 558 and directional light emission regions 558'.

In at least some embodiments, conductors (not shown) extending from terminals (not shown) of the adapter 760 can be coupled to the light source 778 to power the light source 778. In at least some embodiments, the fiber optic 733 is slidably movable relative to the port 775 so that the length of the fiber optic 733 disposed within the lead 180 can be adjusted in a manner similar to that illustrated in FIGS. 6A and 6B. This can be used to adjust the position of emission regions or directional emission regions on the fiber optic 773 relative to the lead. In at least some embodiments, the adapter 760 may include a retention block and fastener (similar to that illustrated in FIG. 1A) on the proximal portion of the connector 762 to fasten against the fiber optic 733 and hold the fiber optic 733 in place and prevent or reduce sliding of the fiber optic relative to the lead 180 after the desired fiber optic position has been selected. In at least some embodiments, an anchor or anchoring sleeve or suture or other arrangement may be positioned around the portion of the fiber optic 733 outside the connector housing 766 and attached to patient tissue to prevent or reduce movement of the fiber optic. In other embodiments, the fiber optic 733 may not be slidably movable through the port 775, but instead may be fixed in relation to the port 775 and connector housing 766.

As an alternative, the fiber optic 733 can terminate in the connector lumen (for example, at the proximal end of the connector lumen at the position corresponding to light source 178 in FIG. 2). The terminal end of the fiber optic 733 can act as a light source (for example, as light source 178 in FIG. 2) for an optical stylet 332, 532, 532a-532e disposed in the lead 180, as described above.

In at least some embodiments, instead of being inserted into the lead 780, the fiber optic 733 may remain outside the lead and implanted next to the lead or elsewhere in the tissue to provide optical stimulation at a desired location in the tissue. Some embodiments may include more than one fiber optic, such as, but not limited to, one, two, three, four, six, eight, or more fiber optics which may be positioned within the lead or outside the lead or any combination thereof.

In at least some embodiments, the optical stylet 332, 532, 532a-532e or fiber optic 733 has at least one radiopaque marker disposed thereon to aid in fluoroscopic visualization of the position of the optical stylet or fiber optic. In at least some embodiments, the optical stylet 332, 532, 532a-532e or fiber optic 733 may include one or more lenses, diffusers, or other optical components to aid or alter the light emission. In at least some embodiments, multiple adapters 160, 760 may be used in series to provide multiple light sources which may be the same or different.

In at least some embodiments, the light source 178, 778 may utilize conductors from two of the terminals of the adapter 160, 760 which may result in two fewer active electrodes on the lead 180. For example, an adapter 160, 760 with eight terminals may only be capable of powering six independent lead electrodes as the other two terminals are used to power the light source 178, 778. In at least some embodiments, the adapters 160, 760 (with an optical stylet 332, 532, 532a-532e or fiber optic 733 or any combination thereof) can be used with existing control modules and leads of an electrical stimulation system to add optical stimulation capability without altering the existing control module or lead (other than to optionally reduce the number of active electrodes in order to power the light source in the adapter).

In at least some embodiments, a lead 180 may be open at the distal end to permit a distal portion of the optical stylet 332, 532, 532a-532e or fiber optic 733 to extend out of the lead.

In at least some embodiments, when implanting the control module 146, the adapter connector 162, 762 may be implanted at a same anatomical space as the control module or a different anatomical space. In at least some embodiments, the adapter 160, 760 can be implanted using the same surgical tools as implantation of the control module 146 and lead 180.

Although the leads described above can provide both electrical stimulation and optical stimulation, it will be understood that the leads, systems, arrangements, and methods can be modified to provide an optical stimulation lead without electrical stimulation by, for example, omitting, removing, or not employing the components, such as electrodes or elements that provide current to the electrodes, for electrical stimulation.

Figure 8:
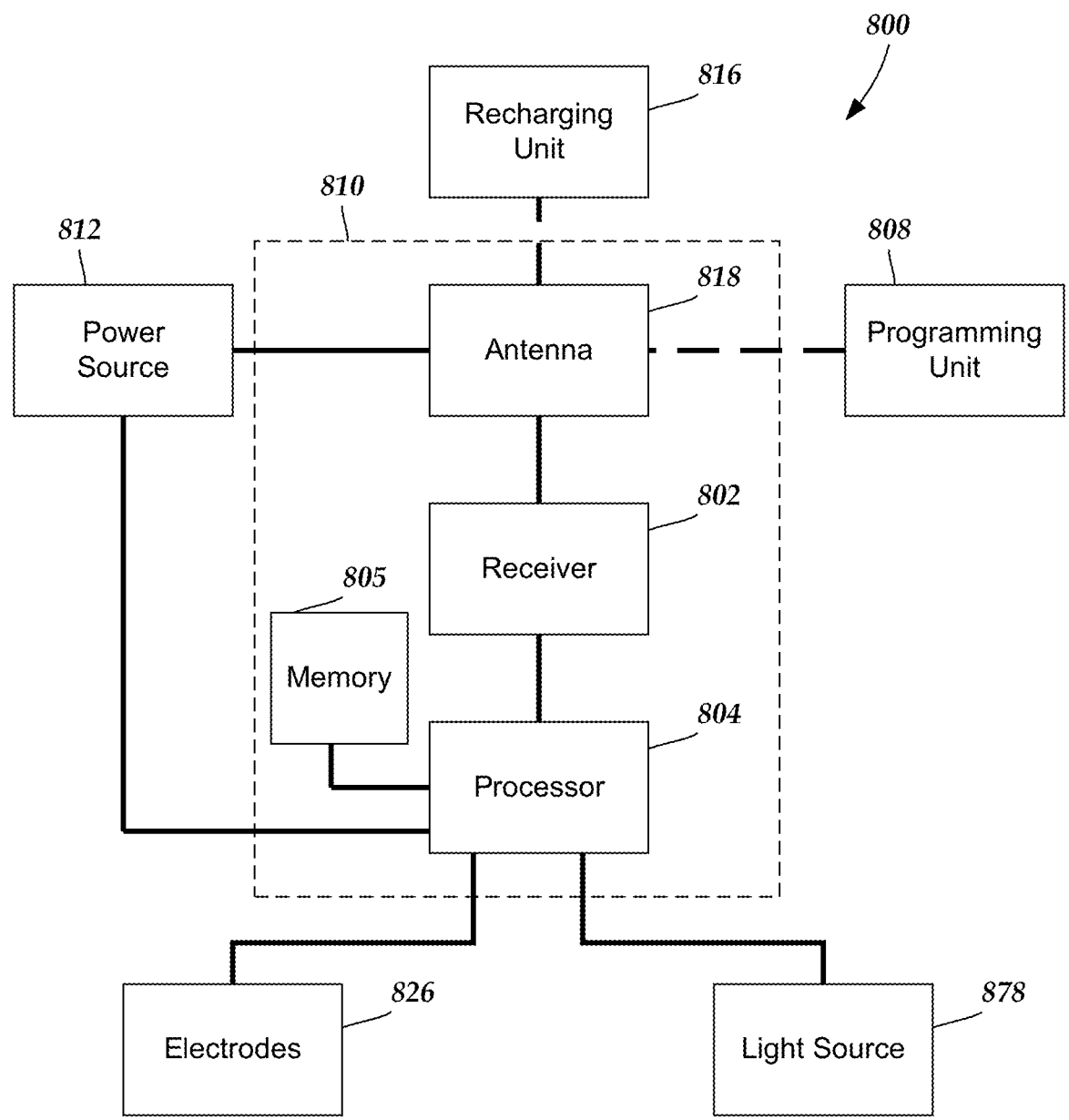
FIG. 8 is a block diagram of one embodiment of a system for electrical/optical stimulation.

FIG. 8 is a schematic overview of one embodiment of components of an electrical/optical stimulation system 800 including an electronic subassembly 810 disposed within a control module (for example, an implantable or external pulse generator). It will be understood that the electrical/optical stimulation system can include more, fewer, or different components and can have a variety of different configurations including those configurations disclosed in the stimulator references cited herein.

In at least some embodiments, selected components (for example, a power source 812, an antenna 818, a receiver 802, a processor 804, and a memory 805) of the electrical/optical stimulation system can be positioned on one or more circuit boards or similar carriers within a sealed housing of a control module. Any suitable processor 804 can be used and can be as simple as an electronic device that, for example, produces signals to direct or generate electrical/optical stimulation at a regular interval or the processor can be capable of receiving and interpreting instructions from an external programming unit 808 that, for example, allows modification of stimulation parameters or characteristics.

The processor 804 is generally included to control the timing and other characteristics of the electrical/optical stimulation system. For example, the processor 804 can, if desired, control one or more of the timing, pulse frequency, amplitude, and duration of the electrical/optical stimulation. In addition, the processor 804 can select one or more of the electrodes 826 to provide electrical stimulation, if desired. In some embodiments, the processor 804 selects which of the electrode(s) are cathodes and which electrode(s) are anodes.

Any suitable memory 805 can be used. The memory 805 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, magnetic storage devices, or any other medium which can be used to store the desired information and which can be accessed by a processor.

The processor 804 is coupled to a light source 878, such as a light source 178, 778 in an adapter 160, 760 as described above. Any suitable light source can be used including, but not limited to, light emitting diodes (LEDs), organic light emitting diodes (OLEDs), laser diodes, lamps, light bulbs, or the like or any combination thereof. In at least some embodiments, the electrical/optical stimulation system may include multiple light sources. In at least some embodiments, each of the multiple light sources may emit light having a different wavelength or different wavelength range. Any suitable wavelength or wavelength range can be used including, but not limited to, visible, near infrared, and ultraviolet wavelengths or wavelength ranges. In at least some embodiments, the optical stimulation system includes a light source that emits in the orange, red, or infrared wavelength ranges (for example, in the range of 600 to 1200 nm or in the range of 600 to 700 nm or in the range of 610 to 650 nm or 620 nm or the like.) In at least some embodiments, the optical stimulation system includes a light source that emits in the green or blue wavelength ranges (for example, in the range of 450 to 550 nm or in the range of 495 to 545 nm or the like.) A wavelength or wavelength range of a light source may be selected to obtain a specific therapeutic, chemical, or biological effect.

Any power source 812 can be used including, for example, a battery such as a primary battery or a rechargeable battery. Examples of other power sources include super capacitors, nuclear or atomic batteries, fuel cells, mechanical resonators, infrared collectors, flexural powered energy sources, thermally-powered energy sources, bioenergy power sources, bioelectric cells, osmotic pressure pumps, and the like. As another alternative, power can be supplied by an external power source through inductive coupling via an antenna 818 or a secondary antenna. The external power source can be in a device that is mounted on the skin of the user or in a unit that is provided near the user on a permanent or periodic basis. In at least some embodiments, if the power source 812 is a rechargeable battery, the battery may be recharged using the antenna 818 and a recharging unit 816. In some embodiments, power can be provided to the battery for recharging by inductively coupling the battery to the external recharging unit 816.

In at least some embodiments, the processor 804 is coupled to a receiver 802 which, in turn, is coupled to an antenna 818. This allows the processor 804 to receive instructions from an external source, such as programming unit 808, to, for example, direct the stimulation parameters and characteristics. The signals sent to the processor 804 via the antenna 818 and the receiver 802 can be used to modify or otherwise direct the operation of the electrical/optical stimulation system. For example, the signals may be used to modify the stimulation characteristics of the electrical/optical stimulation system such as modifying one or more of stimulation duration and stimulation amplitude. The signals may also direct the electrical/optical stimulation system 800 to cease operation, to start operation, to start charging the battery, or to stop charging the battery. In other embodiments, the stimulation system does not include the antenna 818 or receiver 802 and the processor 804 operates as initially programmed.

In at least some embodiments, the antenna 818 is capable of receiving signals (e.g., RF signals) from an external programming unit 808 (such as a clinician programmer or patient remote control or any other device) which can be programmed by a user, a clinician, or other individual. The programming unit 808 can be any unit that can provide information or instructions to the electrical/optical stimulation system 800. In at least some embodiments, the programming unit 808 can provide signals or information to the processor 804 via a wireless or wired connection. One example of a suitable programming unit is a clinician programmer or other computer operated by a clinician or other user to select, set, or program operational parameters for the stimulation. Another example of the programming unit 808 is a remote control such as, for example, a device that is worn on the skin of the user or can be carried by the user and can have a form similar to a pager, cellular phone, or remote control, if desired. In at least some embodiments, a remote control used by a patient may have fewer options or capabilities for altering stimulation parameters than a clinician programmer.

Optionally, the electrical/optical stimulation system 800 may include a transmitter (not shown) coupled to the processor 804 and the antenna 818 for transmitting signals back to the programming unit 808 or another unit capable of receiving the signals. For example, the electrical/optical stimulation system 800 may transmit signals indicating whether the electrical/optical stimulation system 800 is operating properly or not or indicating when the battery needs to be charged or the level of charge remaining in the battery. The processor 804 may also be capable of transmitting information about the stimulation characteristics so that a user or clinician can determine or verify the characteristics.

Although the stimulation systems described above can provide both electrical stimulation and optical stimulation, it will be understood that the systems, arrangements, and methods described above can be modified to provide optical stimulation without electrical stimulation by, for example, may omitting, removing, or not employing the components, such as electrodes or elements that provide current to the electrodes, for electrical stimulation.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An adapter for a stimulation system, comprising:
   an adapter body having a distal end and a proximal end;
   a connector disposed on the distal end of the adapter body, the connector comprising:
      a connector body defining a lead port and a connector lumen extending from the lead port for receiving a proximal end of a stimulation lead;
      a plurality of connector contacts disposed in the connector body and arranged along the connector lumen;
      a light source disposed in the connector body; and
      a fiber optic attached to the light source and extending along the connector lumen and out the lead port and configured for insertion into the proximal end of the stimulation lead;
   a plurality of terminals disposed along the proximal end of the adapter body; and
   a plurality of conductors extending along the adapter body and electrically coupling the connector contacts and the light source to the terminals.

2. The adapter of claim 1, wherein the light source is disposed at a proximal end of the connector lumen.

3. The adapter of claim 1, wherein the fiber optic is directly attached to the light source.

4. The adapter of claim 1, wherein the light source is offset from the connector lumen.

5. The adapter of claim 4, wherein the connector body defines a fiber optic port, opposite the lead port, through which the fiber optic extends into the connector lumen.

6. The adapter of claim 1, wherein the fiber optic comprises a core and a cladding disposed around the core and the cladding comprises at least one emission region, wherein an index of refraction of the at least one emission region is greater than an index of refraction of the core.

7. The adapter of claim 6, wherein the at least one emission region comprises at least one directional emission region, wherein the at least one directional emission region extends around no more than 75% of a circumference of the fiber optic.

8. A kit for providing optical stimulation, comprising:
   the adapter of claim 1; and
   an electrical stimulation lead comprising
   a lead body having a distal end portion and a proximal end portion and defining a lumen configured for receiving the fiber optic, wherein the proximal end portion is configured for insertion through the port of the connector and into the connector lumen of the connector;
   a plurality of electrodes disposed along the distal end portion of the lead body;
   a plurality of terminals disposed along the proximal end portion of the lead body; and
   a plurality of conductors extending along the lead body and electrically coupling the electrodes to the terminals.

9. The kit of claim 8, wherein the fiber optic comprises a core and a cladding disposed around the core, wherein the cladding comprises at least one emission region, wherein an index of refraction of the at least one emission region is greater than an index of refraction of the core.

10. The kit of claim 9, wherein the at least one emission region comprises at least one directional emission region, wherein the at least one directional emission region extends around no more than 75% of a circumference of the fiber optic.

11. The kit of claim 8, wherein the light source is disposed at a proximal end of the connector lumen.

12. The kit of claim 8, wherein the fiber optic is directly attached to the light source.

13. The kit of claim 8, wherein the light source is offset from the connector lumen.

14. A system for electrical/optical stimulation, comprising:
   the kit of claim 8; and
   a control module comprising
   a control module connector defining a connector body, a port, and a connector lumen extending from the port for receiving a proximal end of the adapter, the control module connector comprising a plurality of connector contacts disposed in the connector body and arranged along the connector lumen;
   a housing coupled to the control module connector; and
   an electronic subassembly disposed in the housing and electrically coupled to the connector contacts of the control module connector.

15. A method of optically stimulating patient tissue, the method comprising
   providing the adapter of claim 1;
   electrically coupling the adapter to a control module;
   inserting the fiber optic or an optical stylet optically coupled to the fiber optic into a lead;
   implanting the lead into the patient tissue;
   generating optical stimulation from the light source using the control module; and
   delivering the optical stimulation along i) the fiber optic or ii) the fiber optic and the optical stylet to the patient tissue.

16. A kit for providing optical stimulation, comprising:
   an adapter comprising
   an adapter body having a distal end and a proximal end,
   a connector disposed on the distal end of the adapter body, the connector comprising
      a connector body defining a port and a connector lumen extending from the port for receiving a proximal end of a stimulation lead,
      a plurality of connector contacts disposed in the connector body and arranged along the connector lumen, and
      a light source disposed in the connector body,
   a plurality of terminals disposed along the proximal end of the adapter body, and
   a plurality of conductors extending along the adapter body and electrically coupling the connector contacts and the light source to the terminals,
   an optical stylet configured to receive and transmit light from the light source when a portion of the optical stylet is inserted into the connector of the adapter; and
   an electrical stimulation lead comprising
   a lead body having a distal end portion and a proximal end portion and defining a lumen configured for receiving the optical stylet, wherein the proximal end portion is configured for insertion through the port of the connector and into the connector lumen of the connector, wherein the distal end portion is open and configured for allowing the optical stylet to slide in or out of the distal end portion of the electrical stimulation lead,
   a plurality of electrodes disposed along the distal end portion of the lead body,
   a plurality of terminals disposed along the proximal end portion of the lead body, and
   a plurality of conductors extending along the lead body and electrically coupling the electrodes to the terminals.

17. The kit of claim 16, wherein the optical stylet comprises a core and a cladding disposed around the core and the cladding comprises at least one emission region, wherein an index of refraction of the at least one emission region is greater than an index of refraction of the core.

18. The kit of claim 17, wherein the at least one emission region comprises at least one directional emission region, wherein the at least one directional emission region extends around no more than 75% of a circumference of the optical stylet.

19. A system for electrical/optical stimulation, comprising:
   the kit of claim 16; and
   a control module comprising
   a control module connector defining a connector body, a port, and a connector lumen extending from the port for receiving a proximal end of the adapter, the control module connector comprising a plurality of connector contacts disposed in the connector body and arranged along the connector lumen;
   a housing coupled to the control module connector; and
   an electronic subassembly disposed in the housing and electrically coupled to the connector contacts of the control module connector.

20. A method of optically stimulating patient tissue, the method comprising
   providing the kit of claim 16;
   electrically coupling the adapter to a control module;
   inserting the optical stylet into the electrical stimulation lead;
   implanting the electrical stimulation lead into the patient tissue;
   generating optical stimulation from the light source using the control module; and delivering the optical stimulation along the optical stylet to the patient tissue.

\* \* \* \* \*